United States Patent
Johnson et al.

(10) Patent No.: US 10,393,856 B2
(45) Date of Patent: Aug. 27, 2019

(54) USING BLUETOOTH BEACONS TO AUTOMATICALLY UPDATE THE LOCATION WITHIN A PORTABLE GAS DETECTOR'S LOGS

(71) Applicant: Honeywell International Inc., Morris Plains, NJ (US)

(72) Inventors: Kirk William Johnson, Calgary (CA); Mahdi Javer, Calgary (CA); Stephen Mroszczak, Calgary (CA)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 745 days.

(21) Appl. No.: 15/053,812

(22) Filed: Feb. 25, 2016

(65) Prior Publication Data

US 2017/0248681 A1    Aug. 31, 2017

(51) Int. Cl.
*H04W 4/00* (2018.01)
*G01S 5/02* (2010.01)
(Continued)

(52) U.S. Cl.
CPC ........ *G01S 5/0294* (2013.01); *G01N 33/0009* (2013.01); *G01S 5/0063* (2013.01); *G08B 21/14* (2013.01); *H04Q 9/00* (2013.01); *H04W 4/02* (2013.01); *H04W 4/021* (2013.01); *H04W 4/80* (2018.02); *H04Q 2209/40* (2013.01); *H04Q 2209/50* (2013.01)

(58) Field of Classification Search
CPC ...... G01S 5/0294; G01S 5/0063; H04W 4/80; H04W 4/02; H04W 4/021; G01N 33/0009; G08B 21/14; H04Q 9/00; H04Q 2209/40; H04Q 2209/50

USPC ................ 455/456.1, 456.6, 550.1; 340/632
See application file for complete search history.

(56) References Cited

U.S. PATENT DOCUMENTS 9,599,529 B1 * 3/2017 Steele ................ G01N 33/0004
10,088,550 B2 * 10/2018 Johnson ................ G01S 5/0294
(Continued)

FOREIGN PATENT DOCUMENTS

EP          3131008 A1    2/2017
WO     2017146934 A1    8/2017

OTHER PUBLICATIONS

International Application No. PCT/US2017/017748, International Search Report, dated Jun. 2, 2017, 4 pages.
(Continued)

*Primary Examiner* — Danh C Le
(74) *Attorney, Agent, or Firm* — Wick Phillips Gould & Martin, LLP

(57) ABSTRACT

Embodiments relate generally to systems and methods for updating the location information for a gas detector device. A gas detector device may comprise a wireless receiver operable to receive information from one or more wireless beacons. In some cases, the wireless beacons may comprise location information. When the gas detector device receives a wireless beacon, the location information stored on the gas detector device may be updated accordingly. In some cases, the subsequent readings of the gas detector device may be associated with the updated location information. In some cases, the wireless beacons may be located at critical areas within a facility, such as entrances or exits to locations.

17 Claims, 3 Drawing Sheets

(51) Int. Cl.
*H04W 4/80* (2018.01)
*G01N 33/00* (2006.01)
*G01S 5/00* (2006.01)
*H04Q 9/00* (2006.01)
*H04W 4/02* (2018.01)
*H04W 4/021* (2018.01)
*G08B 21/14* (2006.01)

(56) References Cited

U.S. PATENT DOCUMENTS

| | | | |
|---|---|---|---|
| 2011/0037599 A1* | 2/2011 | Johnson, Jr. | H04W 4/043 |
| | | | 340/632 |
| 2011/0043373 A1 | 2/2011 | Best et al. | |
| 2011/0161044 A1 | 6/2011 | Gonia et al. | |
| 2012/0219037 A1* | 8/2012 | Myers | H04B 1/7103 |
| | | | 375/141 |
| 2013/0045759 A1 | 2/2013 | Smith | |
| 2014/0320296 A1* | 10/2014 | Thurber | G08B 21/14 |
| | | | 340/632 |
| 2014/0349707 A1 | 11/2014 | Bang | |
| 2015/0237419 A1 | 8/2015 | Lee et al. | |
| 2015/0351008 A1 | 12/2015 | Mayor | |
| 2016/0334378 A1* | 11/2016 | Maddila | G01N 33/0006 |
| 2016/0381440 A1* | 12/2016 | Davis | H04Q 9/00 |
| | | | 340/870.02 |
| 2017/0047696 A1* | 2/2017 | Li | H01R 13/04 |
| 2017/0193790 A1* | 7/2017 | Cornwall | G08B 21/16 |

OTHER PUBLICATIONS

International Application No. PCT/US2017/017748, Written Opinion of the International Searching Authority, dated Jun. 2, 2017, 9 pages.

Anonymous et al: "LMP91000—Sensor AFE System: Configurable AFE Potentiostat for Low Power Chemical-Sensing Applications". Dec. 31, 2014, Retrieved from the Internet: URL: http://www.ti.com/lit/ds/symlink/lmp91000.pdf [retrieved on May 23, 2017], 36 pages.

International Application No. PCT/US2017/017748, International Preliminary Report on Patentability, dated Aug. 28, 2018, 10 pages.

Europe Patent Application No. 17708034.8, Communication pursuant to Rules 161(1) and 162 EPC, dated Aug. 30, 2018, 3 pages.

* cited by examiner

USING BLUETOOTH BEACONS TO AUTOMATICALLY UPDATE THE LOCATION WITHIN A PORTABLE GAS DETECTOR'S LOGS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous work environments, workers may carry gas detectors with them as they work, to allow for detection of gas exposure. The gas detector may alert the user if exposure limits are reached while the user is wearing the gas detector. Gas detectors may comprise interfaces for communicating with the user, such as displays, lights, buzzers, and input buttons. Gas detectors may be configured with settings for alarms, exposure limits, display settings, light and buzzer settings, etc.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
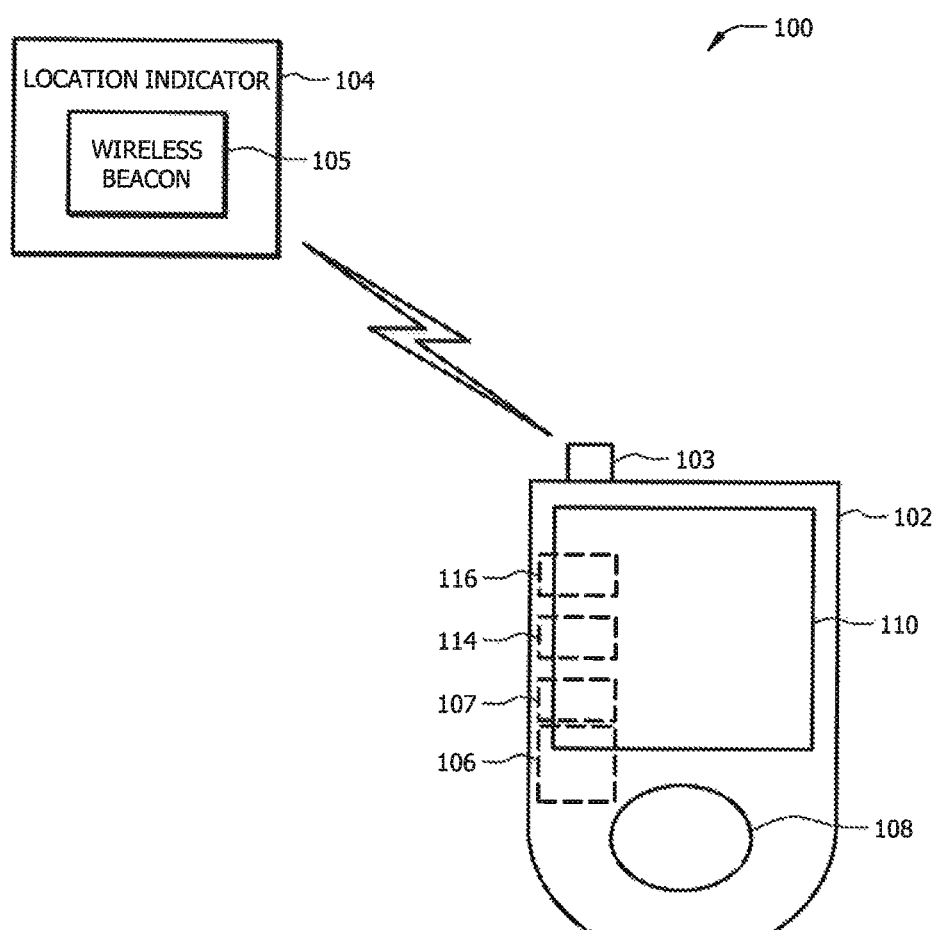
FIG. 1 illustrates a gas detector device according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for updating the location information for a gas detector device. A gas detector device may comprise a wireless receiver operable to receive information from one or more wireless beacons. In some cases, the wireless beacons may comprise location information.

Workers who use gas detectors are sometimes required to indicate their location to the gas detector. For example, the worker may manually enter their current location into the detector. Some detectors may allow a worker to change the location through a series of menus and button presses. Other devices may only have one button and require the user to connect to a computer to change the location. This can be incredibly time consuming for the user.

To simplify the process of updating the location of a gas detector, wireless beacons (such as low power Bluetooth) may be installed at key locations within a facility. These beacons may advertise packets of information with information regarding the location of the beacon, and therefore the user. The user's gas detector may receive these advertisements and automatically update the location field to match the beacon advertisement.

The wireless beacon may be designed to have a very long run time (for example, 2 or more years), and would continuously advertise its location. A gas detector may be designed with a wireless (or BLE) reader that looks for these advertisements, receives the advertisements, and changes its location based on advertisements it sees.

Referring now to FIG. 1, a system 100 is shown, including a gas detector device 102, where the gas detector device 102 comprises a wireless receiver 106. In some embodiments, the gas detector device 102 may comprise one or more sensors 103, a user interface 110, and one or more buttons 108. The gas detector device 102 may be operable to detect, via the sensors 103, any harmful gases or chemicals in the air near a user who is carrying the gas detector device 102. For example, the sensors 103 can detect various types of information such as chemical components of an environment, environmental conditions (e.g., temperature, pressure, wind speed, wind direction, etc.), vibration levels, noise levels, biometric parameters (e.g., heart rate, body temperature, respiration rate; etc.), location including 2-dimensional and/or 3-dimensional position), and the like.

Additionally, the sensors 103 may include, but are not limited to, radiation detectors, smoke detectors, and detectors for determining abnormally low oxygen content in the atmosphere, as well as a wide variety of detectors for detecting chemically hazardous or flammable gases such as, for example, hydrogen sulfide, ammonia, carbon monoxide, natural gas, phosgene, organic compounds (e.g., volatile organic compounds, etc.), and so forth. The gas sensors 103 can also be configured to include integrated wireless communications and the ability to periodically and under event conditions, report the location information, time information, and gas concentration level information wirelessly. In some embodiments, the gas detector device 102 may be operable to alert a user based on the input from the one or more sensors 103. In some embodiments, a user may control the gas detector device 102 and input information via the user interface 110 and/or button 108. Additionally, the user may receive information via the user interface 110.

The gas detector device 102 may also comprise a processor 114 and a memory 116. The The processor 114 may be operable to receive information from the one or more sensors 103. The processor 114 may also be operable to receive information from the wireless receiver 106. In some embodiments, the gas detector device 102 may also comprise a wireless transmitter 107 operable to communicate wirelessly. In some embodiments, the gas detector device 102 may communicate with a remote monitoring station or other remote device. The portable gas detector device 1112 may communicate wirelessly, over a wireless fidelity (Wi-Fi) network, via Bluetooth, Near Field Communication (NFC) or another wireless connection.

The system 100 may also comprise one or more location indicators 104, where the location indicators 104 may be placed at critical or important locations, such as at the entrances and/or exits of specific locations. The location indicator 104 may comprise a wireless beacon 105 operable to broadcast information about the location indicator 104. In some embodiments, the wireless beacon 105 may comprise a Bluetooth (or BLE) wireless beacon. The wireless beacon 105 may be received by the wireless receiver 106 of the gas detector device 102. The wireless receiver 106 may forward the received wireless beacon 105 to the processor 114, where the processor 114 may store the location information from the wireless beacon 105 in the memory 116, and where the processor 114 may associate new information received from the sensors 103 with the updated location information. In some embodiments, the wireless beacon 105 may communicate a location ID, where the gas detector may access a table with the location ID to input information associated with that location ID. In some embodiments, the wireless beacon 105 may communicate a location ID, where the gas detector may simply store the location ID in the memory.

Figure 2:
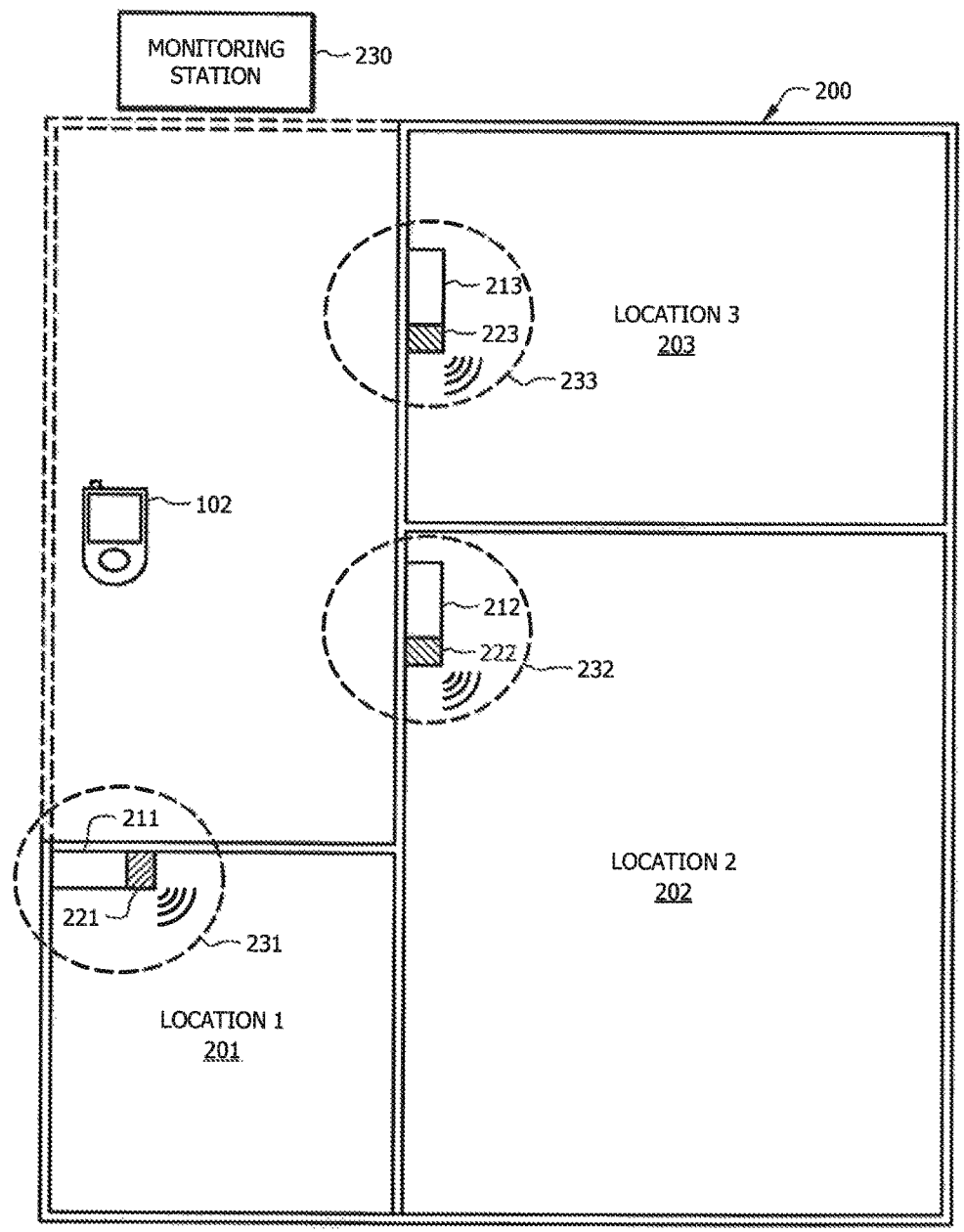
FIG. 2 illustrates a facility map according to an embodiment of the disclosure.

Referring to FIG. 2, a facility 200 is shown comprising multiple locations or zones. The The locations may comprise one or more critical areas, such as entrances or exits. For example, a first location 201 may comprise an entrance 211, a second location 202 may comprise an entrance 212, and a third location 203 may comprise an entrance 213. In some embodiments, the facility 200 may comprise location indicators 221, 222, and 223 located at or near one or more of the entrances 211, 212, 213. The location indicators 221, 222, and 223 may be similar to the location indicator 104 described in FIG. 1, where the location indicators may comprise wireless beacons operable to broadcast information about the location(s).

In some embodiments, the gas detector device 102 may travel, with a user, between the different locations. When the user enters a new location 201, the gas detector device 102 may receive the wireless beacon from the location indicator 221 at the entrance 211 of the location 201. Then, the gas detector device 102 may update the location information stored by the gas detector device 102, where all subsequent readings taken by the (sensors of the) gas detector device 102 may be associated with the updated location information. Similarly, if the gas detector device 102 travels with the user to other locations 202 or 203, the gas detector device 102 may receive new location information from the location indicators 222 and 223, and would update the location information stored on the gas detector device 102 accordingly.

In some embodiments, the gas detector device 102 may indicate to a user that a location update is requested or received, and a user may be required to input a confirmation for the update to proceed. In some embodiments, the location indicators 221, 222, 223 may comprise a physical sign or notification for the user that they are entering a new location and also receiving a wireless beacon to their gas detector device 102.

In some embodiments, the location indicators 221, 222, 223 may have specific ranges 231, 232, 233 that encompass the specific area that is included in the location information in the wireless beacon of the location indicator. For example, the range 231 of the location indicator 221 may be adjusted to cover only the entrance 211 of the location 201, so as not to interfere with other location indicators, or incorrectly indicate the location to a device that is not entering the location 201.

In some embodiments, the gas detector device 102 may also communicate the received location information to a remote monitoring station 230. The remote monitoring station 230 may be monitored by a supervisor, for example. In other embodiments, the location information may be stored locally on the gas detector device 102 and may be accessed later by a monitor or monitoring station.

In some embodiments, a safety communicator (e.g., a communication device) comprising a data collection and communication application may be used to collect the sensor data and communicate the sensor data to the various elements of the system. In some embodiments, the data from the gas detector device 102 can be relayed through a communication module to a server, where the data can be combined to provide an overall view of a worker's risk factor. Various information such as alarms, notifications, information (e.g., maintenance protocols, instructions, live help, etc.), and the like can be relayed back to the worker through the system.

The safety communicator may provide a data connection to a data analytics server and/or a database through a network. The safety communicator may be wirelessly coupled to the network through an access point such as a Wi-Fi, Bluetooth, or cellular connection (e.g., through a wireless service tower). In some embodiments, the network may be the Internet representing a worldwide collection of networks and gateways that use the Transmission Control Protocol/Internet Protocol (TCP/IP) suite of protocols to communicate with one another. In some embodiments, the system 100 may also be implemented as a number of different types of networks such as, for example, an intranet, a local area network (LAN), or a wide area network (WAN).

Figure 3:
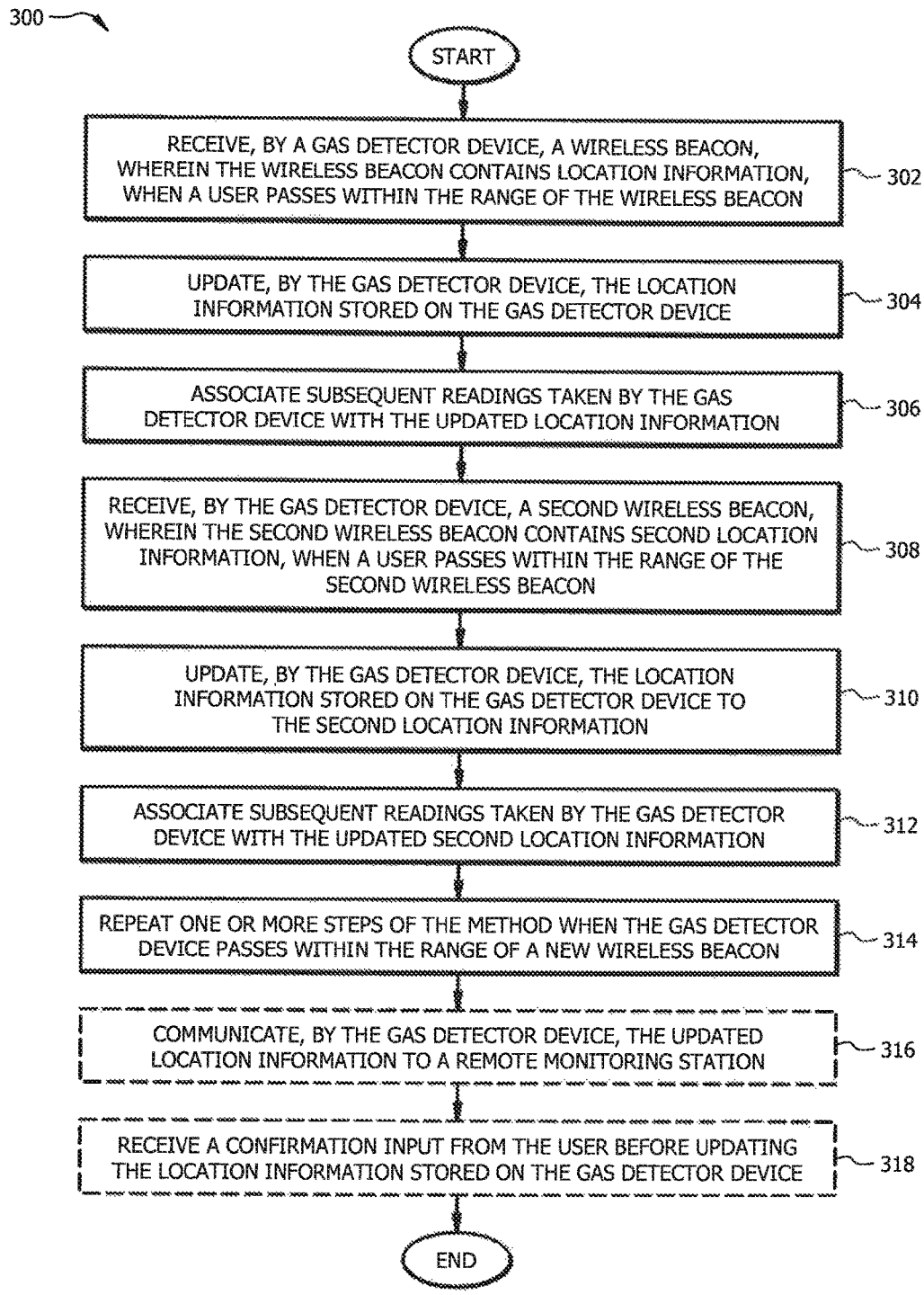
FIG. 3 illustrates a method according to an embodiment of the disclosure.

FIG. 3 illustrates a method for updating the location information on a gas detector device. In some embodiments, one or more steps of the method 300 may occur in different orders than shown in FIG. 3. At step 302, the gas detector device 102 may receive a wireless beacon when the gas detector device passes within the range of the wireless beacon, where the wireless beacon contains location information. At step 304, the gas detector device may update the location information stored on the gas detector device using the location information from the wireless beacon. At step 306, the gas detector device may associate subsequent readings taken by one or more sensors of the gas detector device with the updated location information.

In some embodiments, the gas detector device may receive more than one wireless beacon, where the wireless beacons may be received at different areas within a facility. At step 308, the gas detector device may receive a second wireless beacon, where the second wireless beacon contains second location information, when the gas detector device passes within the range of the second wireless beacon. At step 310, the gas detector device may update the location information stored on the gas detector device using the second location information from the second wireless beacon. At step 312, the gas detector device may associate subsequent readings taken by one or more sensors of the gas detector device with the updated second location information.

In some embodiments, at step 314, one or more steps of the method may be repeated when the gas detector device passes within the range of a new wireless beacon. Optionally, at step 316, the gas detector device may communicate the updated location information to a remote monitoring station. In some embodiments, step 316 may occur after step 304 and/or after step 310. Optionally, at step 318, the gas detector device may receive a confirmation input from the user before updating the location information stored on the gas detector device. In some embodiments, step 318 may occur before step 304 and/or before step 310.

In some embodiments, the wireless beacon may be located at one or more critical areas areas of a facility. In some embodiments, the wireless beacon may be located at one or more entrances to locations within a facility. In some embodiments, the gas detector device may receive the wireless beacon via a wireless receiver incorporated into the gas detector device. In some embodiments, updating the location information stored an the gas detector device occurs automatically.

Some embodiments of the disclosure may comprise a gas detector device comprising one or more sensors operable to detect gases in the air around the gas detector device; a wireless receiver operable to receive one or more wireless beacons; a memory; and a processor operable to receive and store readings from the one or more sensors of the gas detector device; receive location information from the wireless beacons; update the location information stored in the memory of the gas detector device using the received location information; and associate subsequent readings from the one or more sensors with the updated location information.

In some embodiments, the processor may be further operable to receive second location location information from a second wireless beacon; update the location information stored in the memory of the gas detector device using the received second location information; and associate subsequent readings from the one or more sensors with the updated second location information. In some embodiments, the one or more wireless beacons are located at critical areas of a facility. In some embodiments, the one or ore wireless beacons are located at one or more entrances to locations within a facility. In some embodiments, the one or more wireless beacons are incorporated into location indicators. In some embodiments, the location indicators comprise a sign or notification for the user that they are entering a new location, and therefore receiving a wireless beacon to their gas detector device. In some embodiments, the gas detector device may further comprise a wireless transmitter, where the processor is further operable to communicate the updated location information to a remote monitoring station.

In some embodiments, updating the location information occurs automatically. In some embodiments, the processor is further operable to present a confirmation message to the user (via a user interface of the gas detector device); and receive a confirmation input from the user before updating the location information stored on the gas detector device.

Some embodiments of the disclosure may comprise a method for updating the location information on a gas detector device, the method comprising receiving, by a wireless receiver of a gas detector device, a wireless beacon, when the gas detector device passes within the range of the wireless beacon, where the wireless beacon contains location information; updating, by a processor of the gas detector device, the location information stored on the gas detector device using the location information from the wireless beacon; and associating, by the processor of the gas detector device, subsequent readings taken by one or more sensors of the gas detector device with the updated location information.

In some embodiments, the method may further comprise receiving, by the wireless receiver of the gas detector device, a second wireless beacon, when the gas detector device passes within the range of the second wireless beacon, where the second wireless beacon contains second location information; updating, by the processor of the gas detector device, the location information stored on the gas detector device using the second location information from the second wireless beacon; and associating, by the processor of the gas detector device, subsequent readings taken by the one or more sensors of the gas detector device with the updated second location information.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of," Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for updating the location information on a gas detector device, the method comprising:
   receiving, by a gas detector device, a wireless beacon, when the gas detector device passes within the range of the wireless beacon, wherein the wireless beacon contains location information;
   updating, by the gas detector device, the location information stored on the gas detector device using the location information from the wireless beacon;
   associating, by the gas detector device, subsequent readings taken by one or more sensors of the gas detector device with the updated location information;
   receiving, by the gas detector device, a second wireless beacon, when the gas detector device passes within the range of the second wireless beacon, wherein the second wireless beacon contains second location information;
   updating, by the gas detector device, the location information stored on the gas detector device using the second location information from the second wireless beacon; and
   associating subsequent readings taken by the one or more sensors of the gas detector device with the updated second location information.

2. The method of claim 1 further comprising repeating one or more steps of the method when the gas detector device passes within the range of a new wireless beacon.

3. The method of claim 1 further comprising communicating, by the gas detector device, the updated location information to a remote monitoring station.

4. The method of claim 1, wherein the wireless beacon is located at one or more critical areas of a facility.

5. The method of claim 1, wherein the wireless beacon is located at one or more entrances to locations within a facility.

6. The method of claim 1, wherein the gas detector device receives the wireless beacon via a wireless receiver incorporated into the gas detector device.

7. The method of claim 1, wherein updating, by the gas detector device, the location information stored on the gas detector device occurs automatically.

8. The method of claim 1 further comprising receiving a confirmation input from a user before updating the location information stored on the gas detector device.

9. A gas detector device comprising:
   one or more sensors operable to detect gases in the air around the gas detector device;
   a wireless receiver operable to receive one or more wireless beacons;
   a memory; and
   a processor operable to:
      receive and store readings from the one or more sensors of the gas detector device;
      receive location information from the wireless beacons;
      update the location information stored in the memory of the gas detector device using the received location information;
      associate subsequent readings from the one or more sensors with the updated location information;
      receive second location information from a second wireless beacon;
      update the location information stored in the memory of the gas detector device using the received second location information; and
      associate the subsequent readings from the one or more sensors with the updated second location information.

10. The gas detector device of claim 9, wherein the one or more wireless beacons are located at critical areas of a facility.

11. The gas detector device of claim 9, wherein the one or more wireless beacons are located at one or more entrances to locations within a facility.

12. The gas detector device of claim 9, wherein the one or more wireless beacons are incorporated into location indicators.

13. The gas detector device of claim 12, wherein the location indicators comprise a sign or notification for a user that they are entering a new location, and therefore receiving a wireless beacon to their gas detector device.

14. The gas detector device of claim 9 further comprising a wireless transmitter, wherein the processor is further operable to communicate the updated location information to a remote monitoring station.

15. The gas detector device of claim 9, wherein updating the location information occurs automatically.

16. The gas detector device of claim 9, wherein the processor is further operable to:
   present a confirmation message to a user via a user interface of the gas detector device; and receive a confirmation input from the user before updating the location information stored on the gas detector device.

17. A method for updating the location information on a gas detector device, the method comprising:
receiving, by a wireless receiver of the gas detector device, a wireless beacon, when the gas detector device passes within the range of the wireless beacon, wherein the wireless beacon contains location information;
updating, by a processor of the gas detector device, the location information stored on the gas detector device using the location information from the wireless beacon;
associating, by the processor of the gas detector device, subsequent readings taken by one or more sensors of the gas detector device with the updated location information;
receiving, by the wireless receiver of the gas detector device, a second wireless beacon, when the gas detector device passes within the range of the second wireless beacon, wherein the second wireless beacon contains second location information;
updating, by the processor of the gas detector device, the location information stored on the gas detector device using the second location information from the second wireless beacon; and
associating, by the processor of the gas detector device, any subsequent readings taken by the one or more sensors of the gas detector device with the updated second location information.

* * * * *